United States Patent [19]

Kelman

[11] Patent Number: 4,863,465
[45] Date of Patent: Sep. 5, 1989

[54] INTRAOCULAR LENS WITH MULTIPLE-FULCRUM HAPTIC

[76] Inventor: Charles D. Kelman, 269 Grand Central Pkwy., Floral Park, N.Y. 11005

[21] Appl. No.: 12,856

[22] Filed: Feb. 10, 1987

[51] Int. Cl.$^4$ ............................................... A61F 2/16
[52] U.S. Cl. ...................................................... 623/6
[58] Field of Search ........................................... 623/6

[56] References Cited

U.S. PATENT DOCUMENTS

| | | |
|---|---|---|
| 4,092,743 | 6/1978 | Kelman .................................. 623/6 |
| 4,244,060 | 1/1981 | Hoffer ................................... 623/6 |
| 4,249,271 | 2/1981 | Poler ..................................... 623/6 |
| 4,402,579 | 9/1983 | Poler ..................................... 623/6 |
| 4,403,353 | 9/1983 | Tennant ................................. 623/6 |
| 4,418,431 | 12/1983 | Feaster ................................. 623/6 |
| 4,624,670 | 11/1986 | Bechert, II ........................... 623/6 |
| 4,655,775 | 4/1987 | Clasby, III ........................... 623/6 |
| 4,676,794 | 6/1987 | Kelman ................................. 623/6 |

Primary Examiner—Ronald L. Frinks
Attorney, Agent, or Firm—Henry Sternberg; Bert Lewen

[57] ABSTRACT

An intraocular lens for implantation within an eye after cataract surgery. The intraocular lens has a haptic having an elongated gently curving seating portion having a free end and a weakened portion about which such seating portion pivots. The weakened portion is spaced from the fulcrum formed at the location at which the haptic is anchored to the lens body such that the free end of the seating portion moves toward the lens body in response to compression of the seating portion toward the lens body for facilitating seating thereof, while minimizing the risk of injury to the delicate membranes in the eye by outwardly extending distal portions of the haptics. The construction of the lens being such that except for the weakened portion of the haptic, the entire haptic, including the seating portion, would pivot about the point of connection of the haptic to the lens body with the result that the free end portion would move away from, or at least not toward, the lens body, in response to such compression of the seating portion.

12 Claims, 2 Drawing Sheets

INTRAOCULAR LENS WITH MULTIPLE-FULCRUM HAPTIC

BACKGROUND OF THE INVENTION

In opthalmic surgery, following removal of the natural lens of the eye, an intraocular lens is implanted to take the place of the lens removed. Lenses designed to be placed in the posterior chamber may be implanted in either the ciliary sulcus or the capsular bag of the eye. Various types of such lenses have been proposed and are in use. For example, U.S. Pat. No. 4,159,546 discloses an intraocular lens supported by a plurality of flexible strands secured to the lens body. Another lens design is the so called "Simcoe Posterior Chamber Lens" sold by Cilco Inc. as their "S2" posterior chamber lens. The latter has long strands which gently curve from the point of connection to the free ends thereof.

Although great advances have been made over the years in intraocular lenses, the prior art designs are not without their problems. The Simcoe style prior art lenses (see FIG. 1) have very long, gently curving, loops which exert gentle pressure and are easily compressible, but, because of the length of the loops, the free ends thereof tend to move outwardly, i.e., away from the lens body, in response to compression. This type of lens, therefore, requires substantial intraocular manipulation to move it from the anterior chamber into position in the posterior chamber, so as to avoid injury to the delicate tissue in the eye, by the outwardly extending free ends of the haptics.

Each support strand of such prior art structure generally pivots about the point at which such support strand is anchored to the lens body, i.e., typically a point "P" on, or close to, the periphery of the lens body. Thus, generally radial pressure on the elongated seating portion of the support strands, such as is typically applied for manipulating the lens through the pupil and seating it in the posterior chamber, causes the free ends of the strands to move away from, or at least not toward, the lens body. Consequently, increased intraocular manipulation is required to move the lens, having these outwardly extending free ends of the haptics, into the posterior chamber without damaging the delicate membranes within the eye and it is particularly difficult to safely manipulate these outwardly extending free ends into the capsular bag.

U.S. Pat. No. 4,624,670, issued to Bechert on Nov. 25, 1986, discloses an intraocular lens having a pair of loops which extend from opposite sides of the lens body. Each of the loops includes a notch disposed generally mid-way along the curved seating portion of the loop in question. The notches are said to divide the seating portions so as to simulate a four-point fixation in the eye and at the same time facilitate insertion by reducing the possibility of slippage of the inserting instrument. The Bechert lens is shown to have haptics which pivot generally about their point of connection to the lens body, in response to compression of the haptic preparatory to seating thereof. The free ends of the haptics of Bechert, therefore, will move outwardly rather than inwardly with respect to the lens body in response to such compression.

If an effort is made to move the outwardly extending free ends of the haptics of such the prior art lenses toward the lens body, there is likely a substantial tendency for the lens body to rotate due to the location of the fulcrum, i.e., at the point of connection between the haptic and the lens body. Increased manipulation within the eye is therefore likely to be necessary in order to avoid such rotational movement of the lens body. Such added manipulation, of course, in addition to requiring substantial skill and being time consuming, increases also the risk of injury to the eye.

The present invention avoids these problems by allowing each lens support strand to be compressed toward the lens body by substantially the full amount required for moving the lens into the posterior chamber without resulting in an outward movement, i.e., a movement away from the periphery of the lens body, of the free ends of the lens support strands.

The lens support strands of the present invention preferably have long, gently curving, loops, but unlike those of the prior art, the loops of the present invention are provided with a weakened portion forming a second fulcrum located thereon at a location spaced from the lens body, i.e., intermediate the location at which the strand is anchored to the lens body (hereinafter "first fulcrum") and the elongated seating portion of the strand. The arrangement is such that the seating portion will, in response to generally radial compression thereof by the surgeon, pivot first about the intermediate "second" fulcrum and only finally (if additional compressive forces are exerted) about the first fulcrum. As noted above, the pivoting about such second fulcrum, of the haptics according to the present invention, avoids further outward movement of the free ends of the haptics during the initial compression of the haptics. This offers the advantages of allowing the surgeon to more readily position the lens without the lens body rotating about its axis and without the substantial risk of injury to the delicate tissue within the eye by outwardly extending distal portions of the haptics thus making such positioning and seating much simpler and safer.

SUMMARY OF THE INVENTION

According to one preferred embodiment, the present invention is an intraocular lens for surgical implantation into the human eye and comprises a lens body and two support strands each being in the shape of a long, gently curving, loop. The strands are attached, or anchored, to the lens body at diametrically opposite locations on the periphery of the lens body forming a principal, or first, fulcrum for pivoting of the respective loop and having a second, or intermediate fulcrum, spaced from the first fulcrum so as to be intermediate the lens body and the elongated seating portion of the loop. The loops are radially compressible toward the lens body such that the seating portions, including the free i.e., distal, end of each loop, pivot initially about the intermediate fulcrum causing such distal end to move toward, or at least not away, from the lens body, in response to such radial compression.

DESCRIPTION OF THE DRAWINGS

For the purpose of illustrating the invention, there are shown in the drawings the forms which are presently preferred; it being understood, however, that this invention is not limited to the precise arrangements and instrumentalities shown.

DETAILED DESCRIPTION OF THE INVENTION

Figure 1:
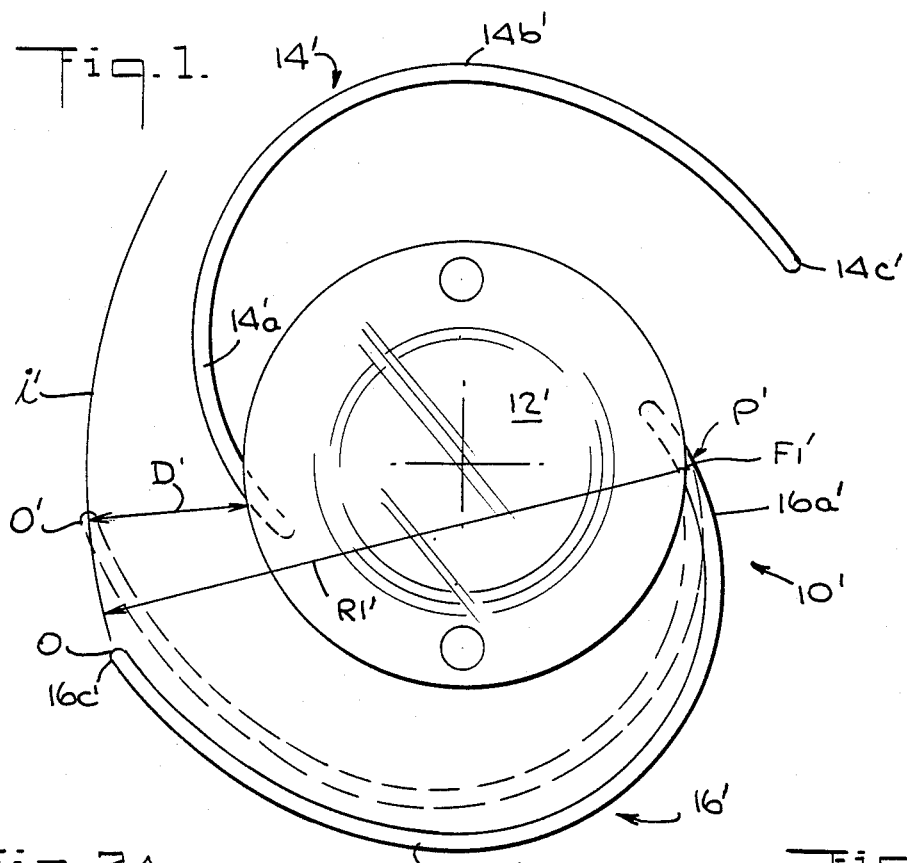
FIG. 1 shows a prior art lens having elongated, gently curving strands, with the inferior strand shown in solid line, in uncompressed condition, and in dashed line in partly compressed condition.

Referring now to the drawings, there is shown in FIG. 1 a intraocular lens 10' according to the prior art, having a lens body 12' and a pair of strands 14' and 16', which strands support the lens body when it has been implanted.

Once implanted, the lens body is supported and held in place by a plurality of support strands. Two of such strands, 14' and 16' are used, each one being attached or secured adjacent to the peripheral lens body edge and on opposite sides thereof. The strands are flexible, that is they yield under pressure, and also have a memory retaining feature whereby the strand will return to its normal, extended, position or will automatically tend to do so once the pressure has been released. Thus, the strands have a spring-like quality.

The strands are attached to the lens body by adhesive or other mechanical means adjacent to the periphery of the lens body so as to have minimum interference with the lens body itself.

As seen in FIG. 1, each of the strands 14' and 16' has a first, or connecting, portion 14a', 16a' adjacent to the point of connection P' of the respective strand with the lens body and a gently curved or arced seating portion 14b', 16b', terminating in a free end 14c', 16c'. The curved seating portions 14b', 16b' have a very long gently curving shape, the curvature of which broadly matches the respective arc of contact within the ciliary sulcus or within the capsular bag for distributing pressure evenly over a large surface area to avoid single-point pressure.

The arced, i.e., gently curving, portions present a rounded strand surface abutting the ciliary body or capsule when the lens is implanted in the posterior chamber. Further, distal ends 14c', 16c' of the strands are located radially outwardly of the lens body 12' at a radius R1' from the point of connection P' of the strand with the lens body. Flexure of the strands, by the surgeon prior to and during implantation, will be a generally radial compression of portions 14b', 16b' resulting in pivoting of the entire strand 14', 16' about its anchor point, or fulcrum, P', from the underformed position shown in solid line to and beyond the partly deformed condition shown in dashed line in FIG. 1. The imaginary arc "i'" drawn from P' as its center, generally represents the path along which distal end 16c' of the haptic 16' of the prior art lens in FIG. 1, moves in response to compression of the seating portion 16b' of such prior art lens. It will be seen that such movement is not toward the lens body 12'. Thus, unsecured end 16c' of the strand 16' will move to a position generally indicated at 0', which is laterally substantially spaced from the lens body. Consequently, the free end 16c' is in a position in which it is readily pointed toward, and thus jabbed against, the delicate tissue within the eye during implantation and in fact makes implantation more difficult since it extends far beyond the periphery of the lens body and thus increases the effective size of the lens which has to be moved through the pupil and into the capsular bag.

Figure 2A:
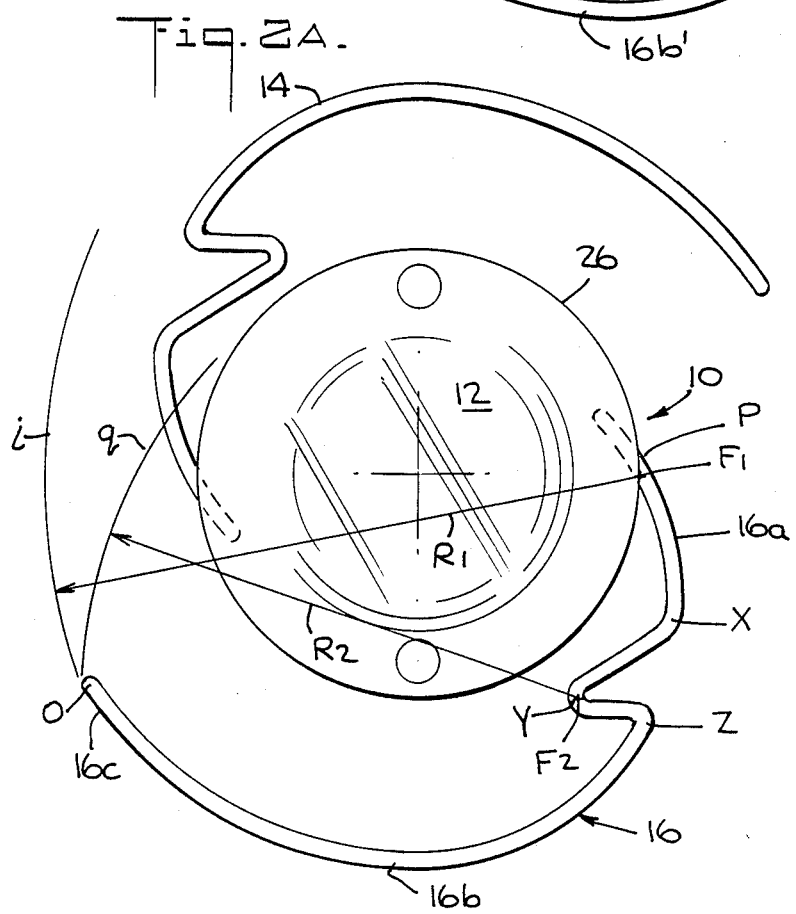
FIG. 2A is a front elevation of a lens in accordance with one preferred embodiment of the present invention.
Figure 2B:
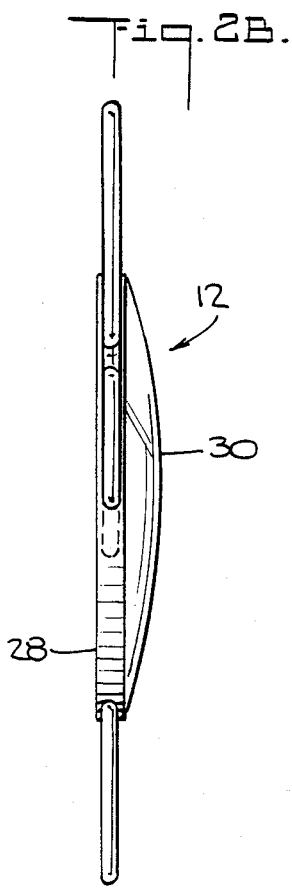
FIG. 2B is a side elevation of the lens shown in FIG. 2A.
Figure 3:
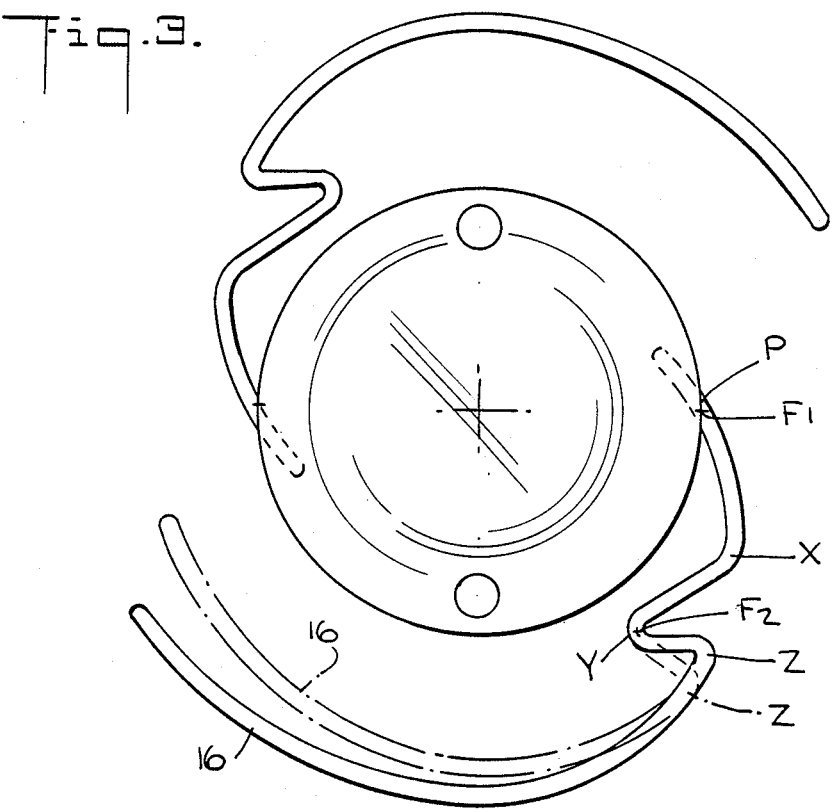
FIG. 3 shows the lens of FIG. 2A with the inferior strand shown in uncompressed condition in full line and in partly compressed condition in dashed lines.

FIGS. 2A and 2B illustrate one preferred form of the lens of the invention, generally indicated by numeral 10, with supporting strand 16 being illustrated in FIG. 3 in solid lines in its natural, undeformed, state and in dashed lines in a position as it might be forced under pressure. It will be observed that, unlike support strands of prior art lenses, the free end 16c of support strands according to the present invention will move toward the lens body, in response to compression of the seating portion radially toward the center of the lens body.

Figure 5A:
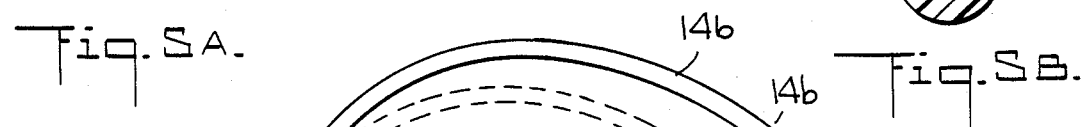
FIG. 5A is a transverse sectional view, according to one preferred embodiment of the present invention, taken along the line A—A of FIG. 4, in the direction of the arrows.
Figure 5B:
FIG. 5B is a transverse sectional view taken along the line B—B of FIG. 4, in the direction of the arrows.

A preferred shape of the lens body 12 is illustrated in FIG. 2B in which the anterior lens body surface 30 is convex while the posterior surface 28 is flat or planar. The lens body peripheral edge 26 is shown to be circular, which is the preferred shape although any other desirable lens body surface and edge shape may be used and those shown are by way of illustration only. According to one preferred embodiment of the invention, seen in FIG. 2A, the strands 14 and 16 are each formed with an inwardly crimped portion, for example, forming a generally V-shaped notch X, Y, Z in the strand. Such notch, preferably faces inwardly with respect to the convex outer contour of the strand and forms a weakened portion exhibiting a fulcrum F2 at the apex "Y" thereof. The notch is preferably formed in the strand at a location intermediate the connecting portion 16a (P-X) and the gently curving seating portion 16b (Z-O). Consequently, seating portion Z-O of the strand, including the free end "O" thereof, will, in response to generally radial compressive pressure applied thereto near the mid-point of the seating portion, pivot about the fulcrum F2, of weakened portion X, Y, Z, well before any pivoting action takes place about the fulcrum F1 defined by connecting point P. Such pivoting action will result in the free end O traversing a path generally shown by an arc "q" drawn with a radius R2 having its center at fulcrum F2 defined by point "Y". Preferably, the strand portion forming the notch X, Y, Z will be of a different cross-sectional shape than the remaining portions of the strand for providing a relatively weakened portion for facilitating flexure of the seating portion Z-O about the fulcrum F2 well before any flexure about fulcrum F-1 takes place. Preferably such cross-sectional shape of the weakened portion at Y will be ribbon-like, or at least elliptical (FIG. 5A) as compared to a preferably round cross-sectional shape (FIG. 5B) for the remaining portions of the strand.

A preferred strand material to achieve the desired results and used in a preferred lens according to the present invention, comprises polypropylene. One preferred strand composition is a proprietary polypropylene known as "Prolene". The lens body 12 may be of any suitable material, preferably a plastic such as a composition which comprises polymethyl methacrylate.

As seen in FIG. 3, the free ends 14c, 16c of the strands 14 and 16 of a lens according to a preferred embodiment of the present invention, move closer to the lens body under compression. This enables the lens according to the invention to be more readily and safely inserted through the pupil of an eye and positioned in the capsular bag. Upon strand 16 moving to its compressed state (dashed line in FIG. 3) its lateral dimension, it will be seen, does not extend beyond the diameter of the lens body 12 by as substantial a distance as the prior art lens. As noted above, this feature allows the surgeon much greater flexibility in positioning and in seating the lens.

Figure 4:
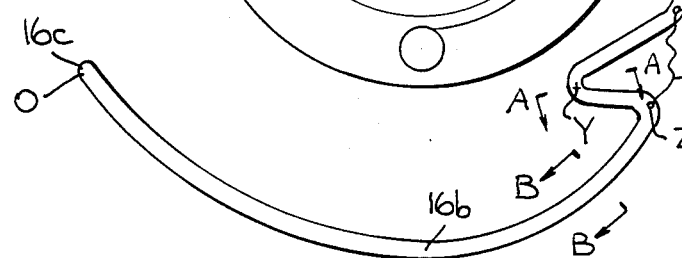
FIG. 4 shows another embodiment of a lens in accordance with the present invention, showing the superior strand in uncompressed condition, in solid line, and in partly compressed condition in dashed lines (the lens of FIG. 4 is identical to that of FIG. 2A except for the added suture 30)

According to another preferred embodiment of the invention illustrated in FIG. 4, the haptics 14, 16 having a weakened region in the form of a V-shaped notch X, Y, Z, of the type described above, have a loose, string-like flexible connecting member 30 bridging the gap formed by the V-shaped notch. The member 30 may be a thread of material such as the material typically used for suturing the eye and may be tied, or otherwise connected to the haptic at points X and Z respectively. The material of the suture 30 is preferably generally inextensible and of such length that the thread 30 will be fully extended (as shown by dashed lines in FIG. 4) upon such compression of the superior haptic as results in pivoting seating portion 14b about fulcrum "Y" to move distal end 14c substantially toward the lens body 12 (to a position such as seen in dashed lines in FIG. 4). Once the suture 30 is fully extended, as seen in dashed lines in FIG. 4, the haptic portions 14a and 14b act as a cohesive unit and any further radial compression of the haptic results in the haptic pivoting about point P as a fulcrum. At such time, the distal end 14c is, however, sufficiently close to the lens body (see distance "D" in FIG. 4) so as not to exhibit the disadvantageous results exhibited by the prior art lenses (see distance D' in FIG. 1).

The present invention may be embodied in other specific forms without departing from the spirit or essential attributes thereof and, accordingly, reference should be made to the appended claims, rather than to the foregoing specification, as indicating the scope of the invention.

I claim:

1. An intraocular lens suitable for use as an artificial lens in the posterior chamber of an eye, comprising:
   a medial portion including a light-focusing lens body;
   first and second position-fixation means individually joined to said lens body at first and second locations, respectively, and extending outwardly from said lens body for seating in interior portions of the posterior chamber of an eye, the juncture at each of said first and second locations forming a first fulcrum about which the corresponding one of said first and second position fixation means can pivot with respect to said lens body,
   at least one of said position-fixation means comprising a lens support strand of generally circular cross-section having a first portion extending outwardly from the respective first fulcrum, a second portion forming an elongated outwardly convex seating portion for seating in the posterior chamber of an eye and having a free end portion, and a third, weakened portion, intermediate said first and second portions and spaced from said respective first fulcrum to form a second fulcrum for pivoting of said second portion with respect to said first portion, said weakened third portion having a flattened transverse cross-sectional shape, the direction of elongation of such flattened cross-section being substantially parallel to the optical axis of said lens body,
   the width of said lens support strand from side to side being greater than the width of the medial portion of said lens as measured in the same side-to-side direction, and the length and shape of said lens support strand being such that in response to compression toward the center of said lens body of the central region of said second portion of said one position fixation means to pivot said second portion about said first fulcrum said free end portion moves in a direction away from said lens body,
   said location of said second fulcrum being such that in response to compression toward the center of said lens body of the central region of said second portion of said one position fixation means to pivot said second portion about said second fulcrum said free end portion moves in a direction toward said lens body, and
   the relative stiffness of said first and second fulcra being such that pivoting of said second portion will take place substantially only about said second fulcrum and not substantially about said first fulcrum, at least until substantial movement of said free end portion toward said lens body has occurred.

2. An intraocular lens according to claim 1 wherein said lens body has a generally circular periphery and said second portion of said strand is outwardly spaced from and generally parallel in shape to the adjacent portion of said periphery.

3. An intraocular lens according to claim 2, wherein said second portion of said strand has a gentle elongated curvature and the straight line distance between said first fulcrum of said strand and said free end portion exceeds, in uncompressed condition of said position fixation means, the diameter of said lens body.

4. An intraocular lens according to claim 2, wherein the arcuate length of said second portion exceed substantially the arcuate length of the portion of the periphery of said lens body which is parallel and adjacent thereto.

5. An intraocular lens according to claim 1 wherein a pair of radii drawn from the optical axis of said lens body to said first fulcrum and to said free end portion, respectively, subtend an angle of at least 90 degrees.

6. An intraocular lens according to claim 1 wherein the other of said position fixation means is substantially the same shape and construction as said one position fixation means.

7. An intraocular lens according to claim 1, wherein said position fixation means are strands of PMMA.

8. An intraocular lens suitable for use as an artificial lens in the posterior chamber of an eye, comprising:
   a medial portion including a light-focusing lens body,
   first and second position-fixation means individually joined to said lens body at first and second locations, respectively, and extending outwardly from said lens body for seating in interior portions of the posterior chamber of an eye, the juncture at each of said first and second locations forming a first fulcrum about which the corresponding one of said first and second position-fixation means can pivot with respect to said lens body,
   at least one of said position-fixation means comprising a lens support strand having a first portion extending outwardly from the respective first fulcrum, a second portion forming an elongated outwardly convex seating portion for seating in the posterior chamber of an eye and having a free end portion, and a third, weakened portion, intermediate said first and second portions and spaced from said respective first fulcrum to form a second fulcrum for pivoting of said second portion with respect to said first portion, said weakened third portion comprising a pair of strand sections forming a notch extending in direction generally transverse to the adjacent respective first and second portions of said strand, the width of said lens support strand from side to side being greater than the width of the medial portion of said lens as measured in the same side-to-side direction, and the length and shape of said lens support strand being such that in response to compression toward the center of said lens body of the central region of said second portion of said one position-fixation means to pivot said second portion about said first fulcrum said free end portion moves in a direction away from said lens body, said location of said second fulcrum being such that in response to compression toward the center of said lens body of the central region of said second portion of said one position-fixation means to pivot said second portion about said second fulcrum said free end portion moves in a direction toward said lens body, and the relative stiffness of said first and second fulcra being such that pivoting of said second portion will take place substantially only about said second fulcrum and not substantially about said first fulcrum, at least until substantial movement of said free end portion toward said lens body has occurred.

9. An intraocular lens according to claim 8 further comprising string means connecting said adjacent respective portions of said first and second portion of said one position-fixation means at opposite sides of said third portion, respectively, for bridging said notch, said string means being of a length such that said portions are loosely connected when said one position fixation means is in uncompressed condition and said string means become taut in response to substantial pivoting of said second portion of said one position fixation means about said second fulcrum.

10. An intraocular lens according to claim 8 wherein said pair of strand sections extend generally in at least two pre-determined opposite senses with respect to said lens body, said pair of sections each have a first end and a second end, said sections being integrally joined to each other at said first ends thereof to form said second fulcrum and joined at said second ends thereof to said first and second portions of said one position fixation means respectively, said lens further comprising inextensible string means connected at opposite ends thereof to said second ends, respectively, of said pair of sections, said string means being of a length exceeding substantially the distance between said second ends for loosely connecting together said second ends, when said one position fixation means is in uncompressed condition thereof and becoming taut, for tightly connecting together said second ends, in response to substantial pivotal movement of said second portion of said one position fixation means about said second fulcrum thereof.

11. An intraocular lens suitable for use as an artificial lens in the posterior chamber of an eye, comprising:

a light-focusing lens body;

first and second position-fixation means individually joined to said lens body at first and second locations, respectively, and extending outwardly from said lens body for seating in interior portions of the posterior chamber of an eye, the juncture at each said first and second locations forming a first fulcrum about which the corresponding one of said first and second position fixation means can pivot with respect to said lens body, at least one of said position-fixation means comprising a leg having a first portion extending outwardly from said lens body, a second portion forming an elongated outwardly generally convex seating portion for seating in the posterior chamber of an eye and having a free end portion, and a third, weakened portion, intermediate said first and second portions and spaced from said lens body to form a second fulcrum for pivoting of said second portion with respect to said first portion, the length and shape of said leg being such that, in uncompressed condition of said leg, said free end portion is located on an arc of a imaginary first circle whose center is at the corresponding said first fulcrum and having a radius of such length that no part of said first circle intersects said lens body, and said free end portion being located also on an arc of a imaginary second circle whose center is at said second fulcrum, and having a radius such that said imaginary second circle intersects said lens body, whereby said free end portion moves toward said lens body, along a path generally defined by an arc of said second circle, when said second portion pivots about said second fulcrum, the relative stiffness of said first and second fulcra being such that pivoting of said second portion will take place substantially only about said second fulcrum and not substantially about said first fulcrum, at least until substantial movement of said free end portion toward said lens body has occurred.

12. An intraocular lens according to claim 11 wherein the other of said position fixation means is substantially the same shape and construction as said one position fixation means.

* * * * *